United States Patent [19]
Weber et al.

[11] Patent Number: 5,281,202
[45] Date of Patent: Jan. 25, 1994

[54] DEVICE FOR DRAINING A FLEXIBLE FLUID CONTAINER

[75] Inventors: Wolfram Weber, Spiesen-Elversberg; Hans J. Neumann, Niederkirchen; Thomas Scherer, Saarlouis; Bernhard Gläser, Tholey, all of Fed. Rep. of Germany

[73] Assignee: Fresenius AG, Bad Homburg, Fed. Rep. of Germany

[21] Appl. No.: 939,523

[22] Filed: Sep. 3, 1992

[30] Foreign Application Priority Data

Sep. 3, 1991 [DE] Fed. Rep. of Germany ....... 4129271

[51] Int. Cl.$^5$ ............................................. A61M 37/00
[52] U.S. Cl. ................................... 604/132; 222/103; 604/131
[58] Field of Search ............... 604/131, 132, 133, 134, 604/140, 73, 75; 222/95, 103, 105

[56] References Cited

U.S. PATENT DOCUMENTS

| | | | |
|---|---|---|---|
| 4,157,771 | 6/1979 | Smith | 222/103 |
| 4,284,209 | 8/1981 | Barbour | 222/103 |
| 4,525,166 | 6/1985 | Leclerc | 604/133 |
| 4,583,972 | 3/1986 | Hunter, III et al. | 604/133 |
| 4,976,851 | 12/1990 | Tanokura et al. | 222/103 |
| 4,991,743 | 2/1991 | Walker | 222/103 |
| 5,135,646 | 8/1992 | Tanokura et al. | 222/103 |

FOREIGN PATENT DOCUMENTS

| | | |
|---|---|---|
| 3911587A1 | 4/1989 | Fed. Rep. of Germany . |
| 1354252 | 1/1963 | France ...................... 222/103 |

*Primary Examiner*—John G. Weiss
*Attorney, Agent, or Firm*—Townsend and Townsend Khourie and Crew

[57] ABSTRACT

A device is disclosed for draining flexible fluid containers, in particular blood bags which form part of an extracorporeal system in a single needle-type arrangement, having a movable plate (4b) and a fixed plate (4a) in which both plates are configured to confront a flexible fluid container. A force member (14), and a force transfer means (8, 18), are arranged in such a way that the force acting upon the movable plate (4b) increases as the container is drained.

11 Claims, 3 Drawing Sheets

DEVICE FOR DRAINING A FLEXIBLE FLUID CONTAINER

BACKGROUND OF THE INVENTION

The present invention is based on a device for draining flexible fluid containers, in particular blood bags in a single needle arrangement type extracorporeal system as is disclosed in U.S. Pat. No. 4,991,743, and is particularly suited to draining blood bags which form a part of a single needle arrangement-type extracorporeal system.

The single needle technology has long been a standard component in the procedure used in the preservative treatment of blood. Central to this procedure is the withdrawal and reinfusion of the unpurified or purified blood through a single needle, i.e. at a single point of penetration. This procedure is gentle on the containers and is less painful to the patient.

An important requisite for efficient dialysis treatment using the single needle method is the rapid withdrawal and reinfusion of blood so as not to increase inordinately the overall length of treatment.

In dialysis treatment using the single needle method, an important time determining factor is seen in the reinfusion of the purified blood. Normally, the purified blood is collected in a flexible container, then drawn from that container, once the arterial portion of the circulatory system is shut off, and injected through the needle back into the patient's blood circulation. The fluid must flow from the container as rapidly and as evenly as possible.

As a further requisite for efficient dialysis treatment, the pressure throughout the dialysis system must be as consistent as possible. This enables the quantity of treated blood, for example, to be precisely determined, allowing the proper amounts of medication to be added and pump capacities to be adjusted accordingly.

Known devices utilized for this purpose may be ascertained, e.g., from the embodiments described below.

In the aforementioned U.S. Pat. No. 4,991,473 a device is claimed which is capable of controlling the pressure applied to a flexible fluid container. This involves, specifically, a plate to which pressure is applied by means of scissor jacks, and which then transfers this pressure throughout the entire withdrawal phase to the surface of the flexible fluid container. However, this type of pressure control fails to account for pressure variations within the flexible fluid container during fluid withdrawal; nowhere does the referenced patent make reference to the fact that the pressure is adjusted to variations in pressure and volume.

German patent publication DE 39 11 587 A1 discloses a device in which a bag is disposed between two pressure plates, one of which is movable and capable of being actuated. This device is disadvantageous in that it requires a complex pressure monitoring device to be mounted to the pressure plates, necessitating close and lengthy supervision.

The two aforementioned references show that it was heretofore impossible to prevent via simple means undesirable pressure variations that consistently occur as blood is withdrawn from a flexible container.

Thus, reinfusion of purified blood using the single needle technique often produces unequal pressures within the dialysis system which lead to treatment durations that are difficult to monitor. Moreover, the length of treatment increases inordinately because, as the remainder of blood drains from the flexible container, the amount of blood transported per unit time decreases continually due to a decrease in pressure.

The problems surrounding pressure drops are clearly illustrated in FIG. 5. The device as claimed in U.S. Pat. No. 4,991,743, for example, exhibits properties characteristic of a semi-weighted pressure plate. With this device the drop in pressure, relative to the initial flow pressure, reaches ca. 50% by the time the remainder of the blood is being drained from the flexible container, due to the fact that the unchanging force is dispersed over an increasingly larger surface area of the bag which abuts the pressure plates, and with that a drop in pressure (force/surface) results. Under these conditions significant pressure fluctuations within the dialysis system and prolongation of the period required for reinfusion of blood into the patient (decreasing flow rate is a function of decreasing pressure) are unavoidable.

SUMMARY OF THE INVENTION

Thus, the object of the present invention is to provide a simple mechanism for draining flexible fluid containers by means of which fluid is drained completely from the containers at an optimally consistent and rapid flow rate.

The object is achieved utilizing a device of the aforementioned type in which a force transfer means transfers the force received by it from force member in such a way that the force acting on a movable plate increases as the container is drained.

The present device no longer operates on the principal by which a predetermined amount of force is applied to a flexible container, resulting in pressure variations over a period of time. Rather, the device functions in such a way that the amount of force applied to the flexible container is varied using a force transfer means to virtually guarantee a constant amount of pressure.

Thus, the force generated by a force member impacts a force transfer means linked to said force member. As the flexible container is being drained, the force transfer means varies the amount of pressure applied to it according to the quantity of remaining fluid. This quantity controlled variable force acts upon a movable plate which is connected to a fixed plate, and on a flexible container constrained between two such plates. The force applied by the force member is varied according to the amount of fluid in such a way that the flexible fluid container is impacted by a virtually constant pressure both when it is full and when it is nearly empty.

After the container is drained, the flexible container is refilled using a pump connected upstream thereof, thereby again generating a force against the force member, thus permitting the container to be drained once more.

An arrangement of this type ensures a virtually consistent fluid flow during the entire drainage phase, resulting on the one hand in a nearly constant level of pressure within the dialysis system, and on the other hand reducing substantially the amount of time required for reinfusing the purified blood, thus minimizing overall time of treatment that a dialysis patient must undergo.

Moreover, the present device does not require the use of complex, elaborate and costly monitoring devices.

In a preferred embodiment of the present invention a force member in the form of a gas-pressure spring is used to apply pressure by means of two levers actuated by the piston members of the gas-pressure spring, to the movable plate that is hingeably attached to one side of the fixed plate, said levers representing a preferred embodiment of the force transfer system. As blood is being drained, a constant pressure is applied by the piston rods of gas-pressure spring to the flexible container disposed between the fixed and hinged plates. Such pressure is deflected by the lever mechanism to the hinged plate and from there to the flexible container.

In a preferred embodiment of the present invention the gas-pressure spring and its associated levers may be locked in place when the flexible container is to be removed from the space between the fixed and hinged plates, for example, upon completion of the dialysis treatment. Locking is achieved by traversing a lever mounted on the end of the force member which is positioned opposite the force transfer means. By this means the force member and force transfer means are raised high enough to prevent any further force from impacting the flexible container, even as force transfer continues.

In further advantageous embodiments of the present invention the force members may be constructed of various types of springs, though springs having a virtually constant spring force are preferred.

A still further advantageous embodiment of the present invention includes two force transfer systems, each of which are constructed as scissors guides and to which a force is applied by a force member.

A still further advantageous embodiment of the present invention includes a housing which is provided with an opening for removing the flexible container, and in which the floor of the housing is defined by the fixed plate.

In a still further advantageous embodiment the flexible fluid container is positioned between the fixed and hinged plates in such a way that its opening is disposed opposite the abutting hinged plate ends.

BRIEF DESCRIPTION OF THE DRAWINGS

The present invention is described in greater detail based on the following embodiments, with reference to FIGS. 1-5 in which.

DESCRIPTION OF SPECIFIC EMBODIMENTS

Figure 1:
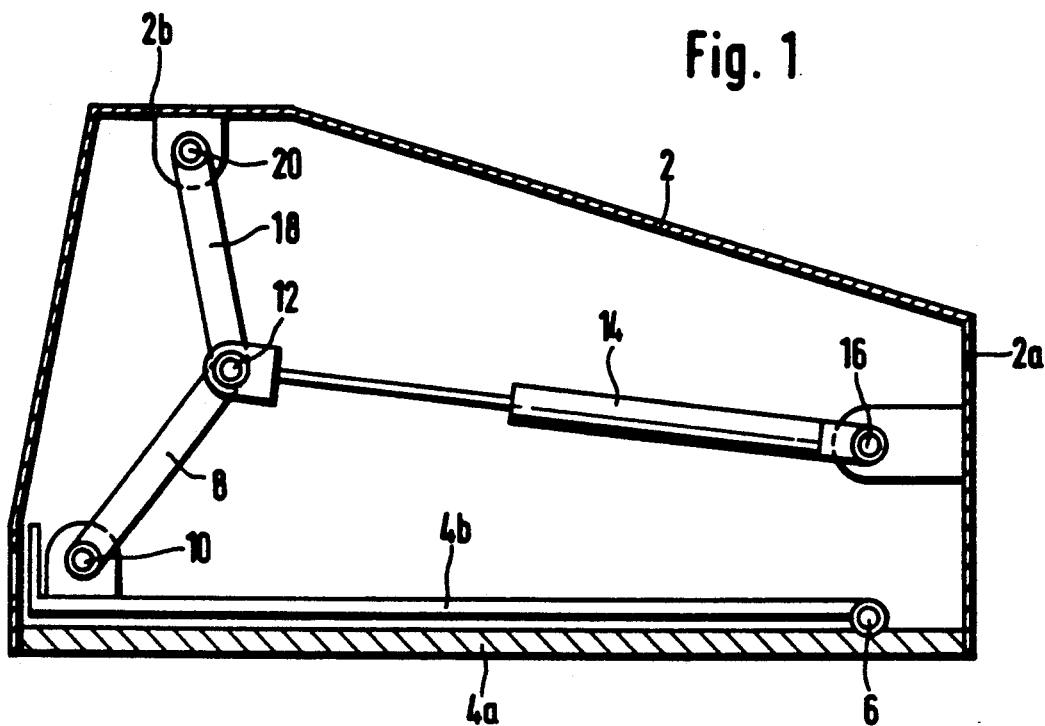
FIG. 1 is a schematic representation of a device for draining a flexible fluid container, shown in the position in which a flexible fluid container (not shown) is drained.

FIG. 1 is a schematic representation of a preferred embodiment of the present invention. Disposed within a housing 2 are a force member, movable plate 4b and fixed plate 4a, force transfer means 8, 18 and flexible fluid container (not shown).

Housing 2 incorporates first a fixed plate 4a and a movable plate 4b which pivots in a range of 0° to a maximum 90° about a hinge 6 relative to fixed plate 4a, with a preferable pivot range of 0° to 25°.

A first lever arm is attached to movable plate 4b and mounted for pivotable movement about a hinge 10. The other end of lever arm 8 is connected to a hinge point 12 which is acted upon at a variable angle by force member 14, in this case a gas-pressure spring. The end of the force member disposed opposite hinge point 12 is attached by a support hinge 16 to the inner wall 2a of the housing. Hinge point 12 is further acted upon by a second lever arm 18 which is also mounted for pivotable movement about hinge point 12, and which also has an opposite end attached by hinge 20 to the upper wall 2b of the housing to be acted on at a variable angle by force member 14.

The force member and force transfer means cooperate in such a way that, as the container is being drained, force is applied by force member 14 through the gas-pressure cylinder piston to hinge point 12. The applied force moves lever arms 8 and 18 from their rest positions and the latter force movable plate 4b in the direction of fixed plate 4a. This in turn causes pressure to be applied to the flexible fluid container (not shown here). The force applied by force member 14 to force transfer means 8, 18 and which is deflected to the movable plate and correspondingly to the flexible fluid container, varies due to the variable angle of the movable hinge point 12 relative to the hinge 20, the hinge 10 and the force member 14 mounted at support hinge 16 in accordance with fluid level in the fluid container, in that as the fluid level drops the force applied by force member 14 to the force transfer means 8, 18 maintains a steady pressure on the flexible fluid container as a result of the intensified leverage effect of the force transfer means. Lever arms 8 and 8 which are actuated by force member 14 are pivoted toward one another, regardless of the amount of force applied to them, at an angle of between 0° and a maximum of 180°, but preferably between 25° and 75°.

Figure 2:
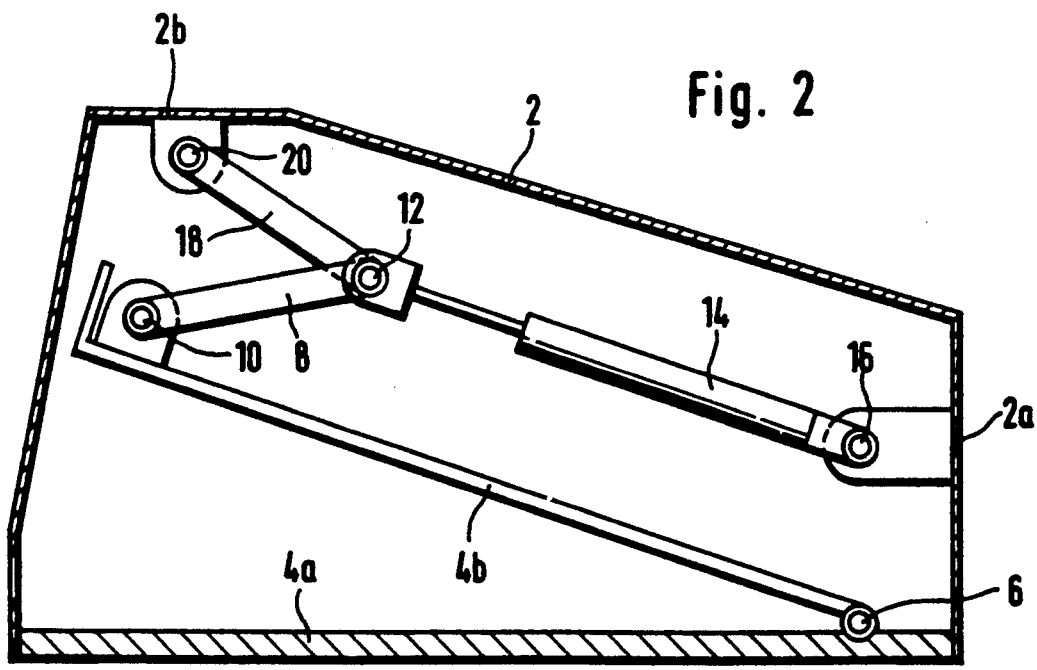
FIG. 2 is a schematic representation of a device for draining a flexible fluid container in accordance with FIG. 1, shown in the position in which a flexible fluid container (not shown) is filled.

FIG. 2 shows the same embodiment of FIG. 1 but with a filled container (not shown here). The container is filled by means of a pump operating against the pressure exerted by the force member. When the container is full, the degree of force exerted by the pressurized force member against hinge point 12 is only slightly varied by an initial minimal deflection of lever arms 8 and 18. The angle between levers 8 and 18 is at this point smaller than when the container is almost completely drained (cf. FIG. 1).

Figure 3:
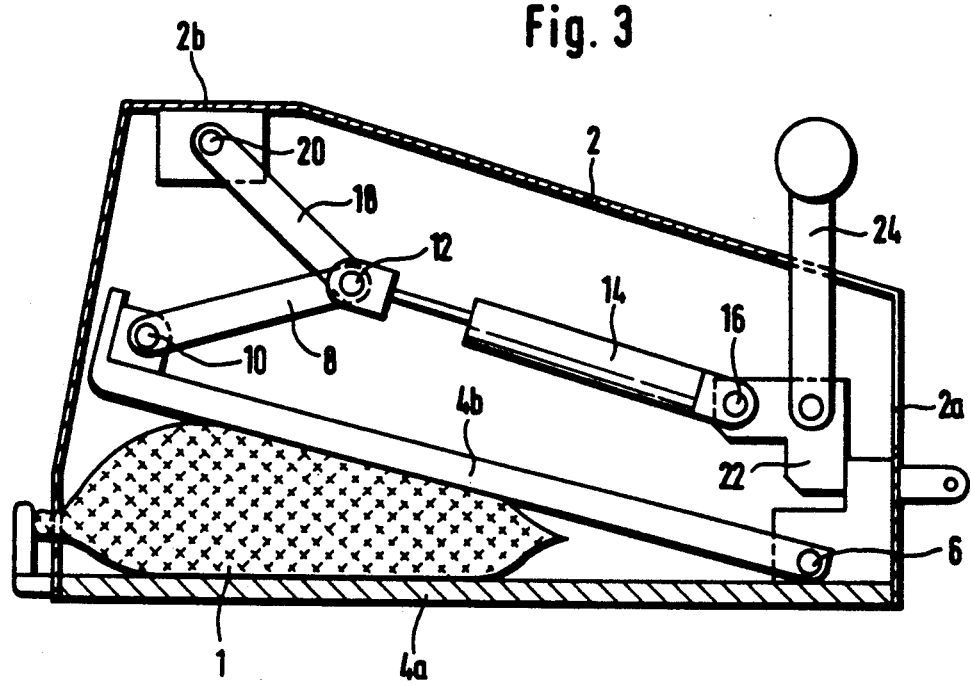
FIG. 3 is a schematic representation of a device for draining a flexible fluid container including a locking mechanism, in which the locking mechanism is in the opened position.

The embodiment of the present invention shown in FIG. 3 includes force members, plates and force transfer means identical to the force members, plates and force transfer means shown in FIGS. 1 and 2. With regard to their operation, therefore, reference is made to the foregoing descriptions.

In addition to the elements shown in FIGS. 1 and 2, the embodiment of FIG. 3 also includes a locking mechanism for force member 14 and force transfer means 8, 18, shown here in the unlocked position. It consists of a locking lever 24 which actuates the locking mechanism and a second lever 22 which, upon actuation of locking lever 24, pivots the force member and force transfer means out of their rest position, thereby preventing them from exerting any pressure on movable plate 4b and, correspondingly on flexible fluid container 1.

Figure 4:
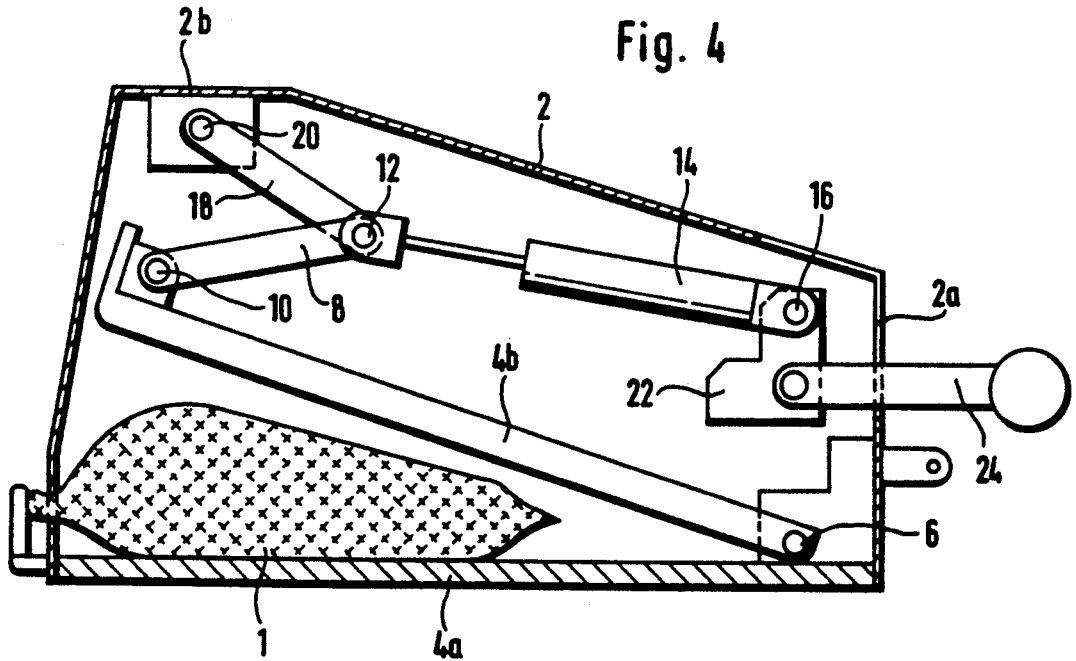
FIG. 4 is a schematic representation of a device for draining a flexible fluid container including a locking mechanism in accordance with FIG. 3, in which the locking mechanism is engaged.

FIG. 4 shows the identical locking mechanism in the locked position. By actuating locking lever 24 the force member and force transfer means were pivoted far enough out of their rest positions to prevent gas-pressure spring 14 from exerting pressure on lever arms 8 and 18, such that movable plate 4b would not be deflected far enough to apply pressure to flexible fluid container 1.

Figure 5:
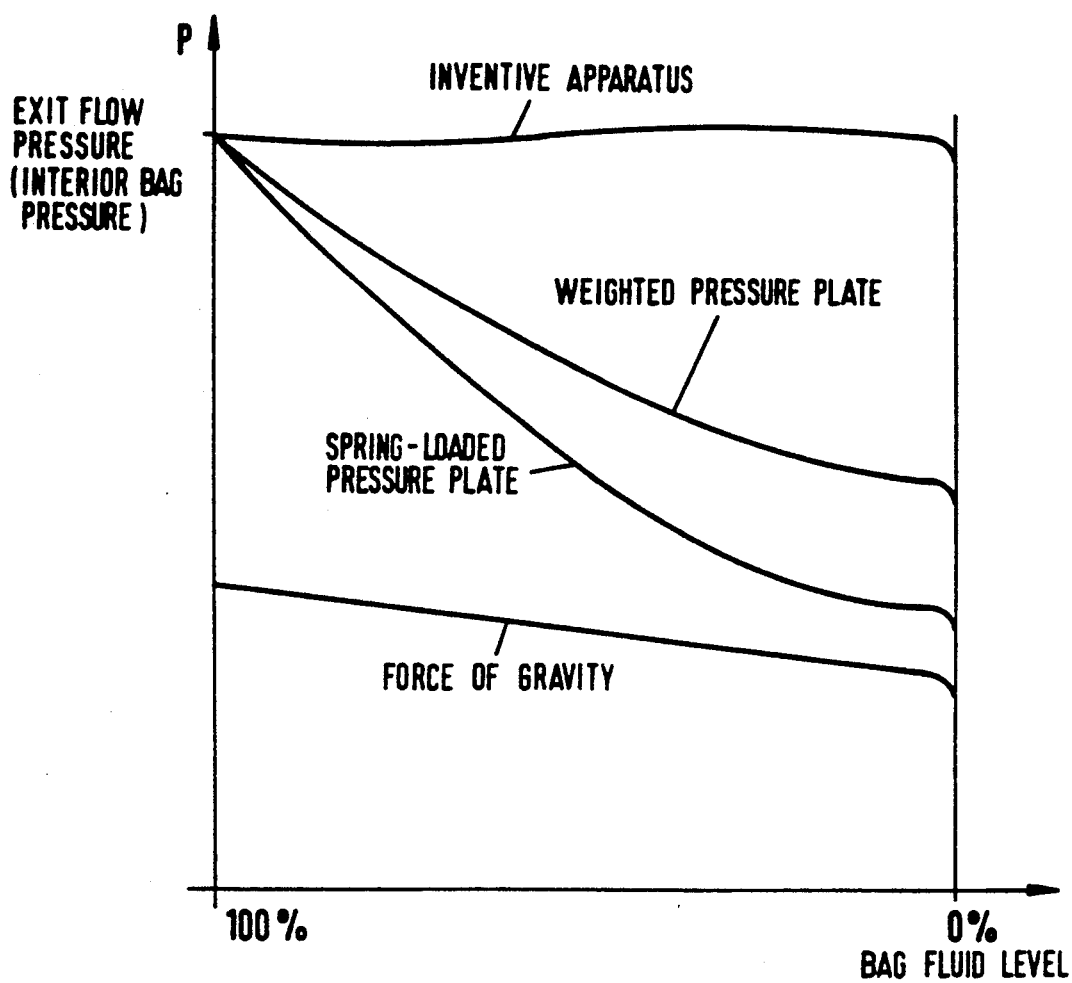
FIG. 5 is a diagram representing the exit flow pressure of the flexible fluid container which is a function of the fluid level in the container, as seen in known devices and as compared to the device of the present invention.

FIG. 5 charts the characteristic curves for the exit flow pressure in various drainage devices. When a flexible fluid container is drained by means of gravitational force only a minimal pressure drop is registered between high and low fluid levels in the container. However, the overall pressure remains low resulting in a minimal fluid flow rate. Fluid containers augmented by spring-loaded or weighted pressure plates are capable of absorbing a higher fluid flow pressure when the fluid level is high, but said pressure, and with that the fluid flow rate, decreases significantly as the fluid level in the container drops. In the device of the present invention which includes a spring mechanism which acts upon a lever, an increased fluid flow pressure is generated when the container is full and can be held virtually constant until the container is completely drained.

While the invention has been particularly shown and described with reference to preferred embodiments thereof, it will be understood by those skilled in the art that the foregoing and other changes in the form and details may be made therein without departing from the spirit or scope of the invention.

What is claimed is:

1. A device for draining flexible fluid containers, in particular blood bags in an extracorporeal system of a single needle arrangement, said device having a first fixed plate (4a), a second movable plate (4b) disposed opposite said fixed plate, in which both plates (4a, 4b) are configured to confront a flexible fluid container (1) therebetween, a force member (14) and force transfer means (8, 18) connected to the second plate (14b), in which the force transfer means (8, 18) is operative to transfer force received by it from said force member (14) in such a way that the force acting on said movable plate (4b) increases as the container is drained, the improvement characterized in that:

one end of the movable plate (4b) is hingeably attached to the fixed plate (4a), and wherein the movable plate (4b) is pivotable counter to the fixed plate (4a) in a range of about 0° to 90°.

2. The device according to claim 1, wherein the force member (14) is a spring means.

3. The device according to claim 1, wherein the force transfer means (8, 18) is defined by a system of levers.

4. The device according to claim 1, wherein a housing (2) is provided with a bottom plate defined by the fixed plate (4a), one end of the force member (14) is attached to a support hinge (16) and another end is connected via a hinge point (12) to force transfer means (8, 18), and wherein the force transfer means deflects force to the movable plate (4b) and to the flexible fluid container (1), the housing having an opening therein.

5. The device according to claim 2, wherein the spring means and an associated push rod are mounted to hinge point (12) at ends of two lever arms (8, 18) that define a system of levers, of which a first lever arm (8) is hingeably attached at its other end to the movable plate (4b) and a second lever arm (18) is hingeably attached at its other end relative tot he fixed plate.

6. The device according to claim 1, wherein a housing (2) is provided fixedly attached to the fixed plate, wherein the spring means has a push rod and is mounted to a hinge point (12) at ends of two lever arms (8, 18) that define a system of levers, of which a first lever arm (8) is hingeably attached at its other end to the movable plate (4b) and a second lever arm (18) is hingeably attached at its other end to the upper wall (2b) of the housing.

7. The device according to claim 6, wherein as the spring means is being released and tensed, both lever arms (8, 18) sweep an angle of between 0° and 180°, preferably between about 25° to 75°.

8. The device according to claim 5, wherein an alternate end of the spring means and the associated pushrod is attached to a support hinge (16) which is a fixed point located on an inner side wall (2a) of a housing.

9. The device according to claim 5, wherein an alternate end of the spring means and the associated pushrod is attached to a support hinge (16) which is disposed on a tipping lever (22) with which the force member (14) and the force transfer means (8, 18) in addition to the second plate (4b) are moved by means of a third lever arm (24) from their respective operating positions.

10. The device according to claim 1, wherein the force member (14) is disposed between two force transfer means upon which it transfers force.

11. The device according to claim 1, wherein the force member (14) is a gas-pressure spring.

* * * * *